United States Patent
Lawless et al.

(10) Patent No.: US 6,231,320 B1
(45) Date of Patent: May 15, 2001

(54) DRUG INFUSION PUMPING CASSETTE LATCHING MECHANISM

(75) Inventors: Michael W. Lawless, Poway; Peter A. Soberon, San Diego; Andrew J. Scherer, San Demas; Stephanie R. Squarcia, Palo Alto, all of CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/302,710

(22) Filed: Apr. 30, 1999

Related U.S. Application Data (63) Continuation-in-part of application No. 09/097,068, filed on Jun. 12, 1998, now Pat. No. 6,142,008.

(51) Int. Cl.⁷ .................................................. F04B 43/08
(52) U.S. Cl. ................................................... 417/477.2
(58) Field of Search ........................................ 417/477.2

(56) References Cited

U.S. PATENT DOCUMENTS

| | | |
|---|---|---|
| 3,699,320 | 10/1972 | Zimmerman . |
| 3,921,622 | 11/1975 | Cole . |
| 3,974,681 | 8/1976 | Namery . |
| 4,068,521 | 1/1978 | Cosentino et al. . |
| 4,114,144 | 9/1978 | Hyman . |
| 4,213,454 | 7/1980 | Shim . |
| 4,217,993 | 8/1980 | Jess et al. . |
| 4,256,437 | 3/1981 | Brown . |
| 4,280,495 | 7/1981 | Lampert . |
| 4,366,384 | 12/1982 | Jensen . |
| 4,367,736 | 1/1983 | Gupton . |
| 4,394,862 | 7/1983 | Shim . |
| 4,418,565 | 12/1983 | St. John . |
| 4,444,546 | 4/1984 | Pazemenas . |
| 4,487,601 | 12/1984 | Lindemann . |
| 4,496,346 | 1/1985 | Mosteller . |
| 4,501,531 | 2/1985 | Bilstad et al. . |
| 4,607,520 | 8/1986 | Dam . |
| 4,658,244 | 4/1987 | Meijer . |
| 4,668,945 | 5/1987 | Aldrovandi et al. . |
| 4,673,334 | * 6/1987 | Allington .............................. 417/53 |
| 4,821,558 | 4/1989 | Pastrone et al. . |
| 4,829,448 | 5/1989 | Balding et al. . |
| 4,884,065 | 11/1989 | Crouse et al. . |
| 4,919,596 | 4/1990 | Slate et al. . |
| 4,981,467 | 1/1991 | Bobo, Jr. et al. . |
| 5,000,663 | 3/1991 | Gorton . |
| 5,026,348 | 6/1991 | Venegas . |
| 5,043,706 | 8/1991 | Oliver . |
| 5,053,747 | 10/1991 | Slate et al. . |
| 5,064,412 | 11/1991 | Henke et al. . |
| 5,176,631 | 1/1993 | Koenig . |
| 5,219,327 | 6/1993 | Okada . |

(List continued on next page.)

FOREIGN PATENT DOCUMENTS

| | | |
|---|---|---|
| 9116087 | 10/1991 | (WO) . |
| 9531233 | 11/1995 | (WO) . |

Primary Examiner—Timothy S. Thorpe
Assistant Examiner—Ehud Gartenberg
(74) Attorney, Agent, or Firm—Beth A. Vrioni; Brian R. Woodworth (57) ABSTRACT

In a pump chassis (112), spring-loaded members (108a, 108b) engage a pumping cassette (114) to it in a predetermined position. The members each include pairs of latches (110a, 110b) that are each beveled to form a ramp so that the latches and associated members are forced outwardly to enable the pumping cassette to be seated within the pump chassis. The latches engage the pump cassette as it is seated, holding it securely. A release button (138) is attached to a spring-loaded shaft (144) that extends into the interior of the pump chassis. The shaft has a ramp formed on its inner end. When the user depresses the release button, the ramp rides under inwardly extending arms (162a, 162b) provided on the members, forcing the members and attached latches to move outwardly. As the members move outwardly, the pumping cassette is released and readily removed.

25 Claims, 6 Drawing Sheets

U.S. PATENT DOCUMENTS

| | | |
|---|---|---|
| 5,343,734 | 9/1994 | Maeda et al. . |
| 5,394,732 | 3/1995 | Johnson et al. . |
| 5,429,485 | 7/1995 | Dodge . |
| 5,537,853 | 7/1996 | Finburgh et al. . |
| 5,601,420 * | 2/1997 | Warner ................................ 417/474 |
| 5,620,312 * | 4/1997 | Hyman ................................ 417/474 |
| 5,752,813 * | 5/1998 | Tyner ................................ 417/477.2 |
| 5,755,691 | 5/1998 | Hilborne . |
| 5,857,843 * | 1/1999 | Leason ................................ 417/477.9 |
| 6,077,246 * | 6/2000 | Kullas ................................ 604/151 |

* cited by examiner

DRUG INFUSION PUMPING CASSETTE LATCHING MECHANISM

This application is a continuation-in-part of U.S. patent application Ser. No. 09/097,068, which was filed on Jun. 12, 1998, now U.S. Pat. No. 6,142,008.

FIELD OF THE INVENTION

The present invention generally relates to a drug infusion pump that employs a pumping cassette, and more specifically, to a mechanism for removably engaging the pumping cassette in a pump chassis.

BACKGROUND OF THE INVENTION

Several different types of pumps are used by medical personnel to infuse drugs into patients. Of these, cassette infusion pumps are often preferred because they provide a more accurately controlled rate and volume of drug infusion than other types of infusion pumps. A cassette pump employs a disposable plastic cassette disposed in the line extending between a drug reservoir and the patient's body. The cassette is inserted into an appropriate receptacle of a pump chassis. The pump chassis provides the driving force that pumps fluid through the cassette and typically includes a microprocessor control programmed to deliver a selected volume of fluid to the patient at a selected rate of flow. In addition, the pump chassis may include one or more pressure sensors and air bubble sensors used to monitor the drug infusion process to protect against potential problems that may arise during the drug delivery.

In prior art designs for the pump chassis, it is common practice to latch a pumping cassette into a receptacle by closing a door over the cassette. When thus closed, the door retains the cassette in a predefined position within the pump chassis. However, the door, its hinges, and its latch tends to add considerable weight and bulk that is a disadvantage in an ambulatory drug infusion system. In at least one prior design for an ambulatory pump chassis, retention of the cassette in its receptacle has required following a four-step process. This prior design employs a sliding cover over the cassette receptacle, with a separate latch for retaining the cassette in the receptacle. Accordingly, to load a cassette into this pump, it is necessary to: (1) press the slide into its open position, (2) open the latch, (3) insert the cassette into its receptacle, and (4) close the slide over the cassette. A corresponding four-step process is also required to remove a cassette from the pump chassis in this pump. Clearly, such a procedure is likely to be considered excessively time consuming and complex when it must be repeated each time that a cassette is engaged in the pump chassis to deliver a drug to a patient.

Thus, it would be preferable to provide a much simpler mechanism for engaging a pumping cassette in a predefined position so that the pump chassis can properly drive the cassette and can monitor pressure and detect any air bubbles in the fluid being administered to a patient. It would be preferable to eliminate any door or slide covering the cassette and to provide a mechanism for unlatching the cassette from the pump chassis with the push of a button. The prior art does not disclose any such mechanism for latching and/or unlatching a cassette in a pump chassis.

SUMMARY OF THE INVENTION

In accord with the present invention, apparatus is defined for engaging a pumping cassette at a predefined position within a pump chassis, for use in delivering fluids to a patient. The apparatus includes a pair of opposed pivotable members disposed at opposite sides of a cavity within the pump chassis; the cavity is sized to receive a pumping cassette. Each opposed member is pivotally mounted to the pump chassis so as to pivot away from and towards the cavity and includes a surface configuration that engages a portion of a pumping cassette, retaining the cassette in the predefined position within the cavity. At least one spring is coupled to the pair of opposed members and applies a biasing force tending to pivot the pair of opposed members towards the cavity. As a pumping cassette is forced into the cavity, interference with the cassette forces the opposed members to pivot outwardly, away from each other and from the cavity. The biasing force causes the surface configuration on each member to engage the pumping cassette after the pumping cassette has been forced into the cavity, retaining the pumping cassette at the predefined position.

A release is also provided, which when activated by an operator, forces the pair of opposed members to pivot outwardly, away from the cavity, thereby releasing a pumping cassette that has previously been inserted and retained within the pump chassis. The release includes a push button that is activated by depressing it, and a tension spring coupled to the push button. The tension spring produces a force tending to bias the push button outwardly from the pump chassis.

The spring that biases the pair of opposed members inwardly preferably extends between the pair of opposed members through the pump chassis.

In one form of the invention, the surface configuration on each of the pair of opposed members includes at least one tab adapted to engage a corresponding slot in the pumping cassette as the pumping cassette is pushed into the cavity. In an alternative embodiment, the tab is adapted to overlie an edge of a pumping cassette as the pumping cassette is pushed into the cavity.

An air bubble sensor is disposed on the pair of opposed members and pivots with them. In this manner, the air bubble sensor is enabled to pivot into contact with a tube connected to a pumping cassette that is retained in the cavity by the pair of opposed members. While not required, in a preferred form of the invention, the air bubble sensors provide an anchor for a spring coupling the pair of opposed members.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
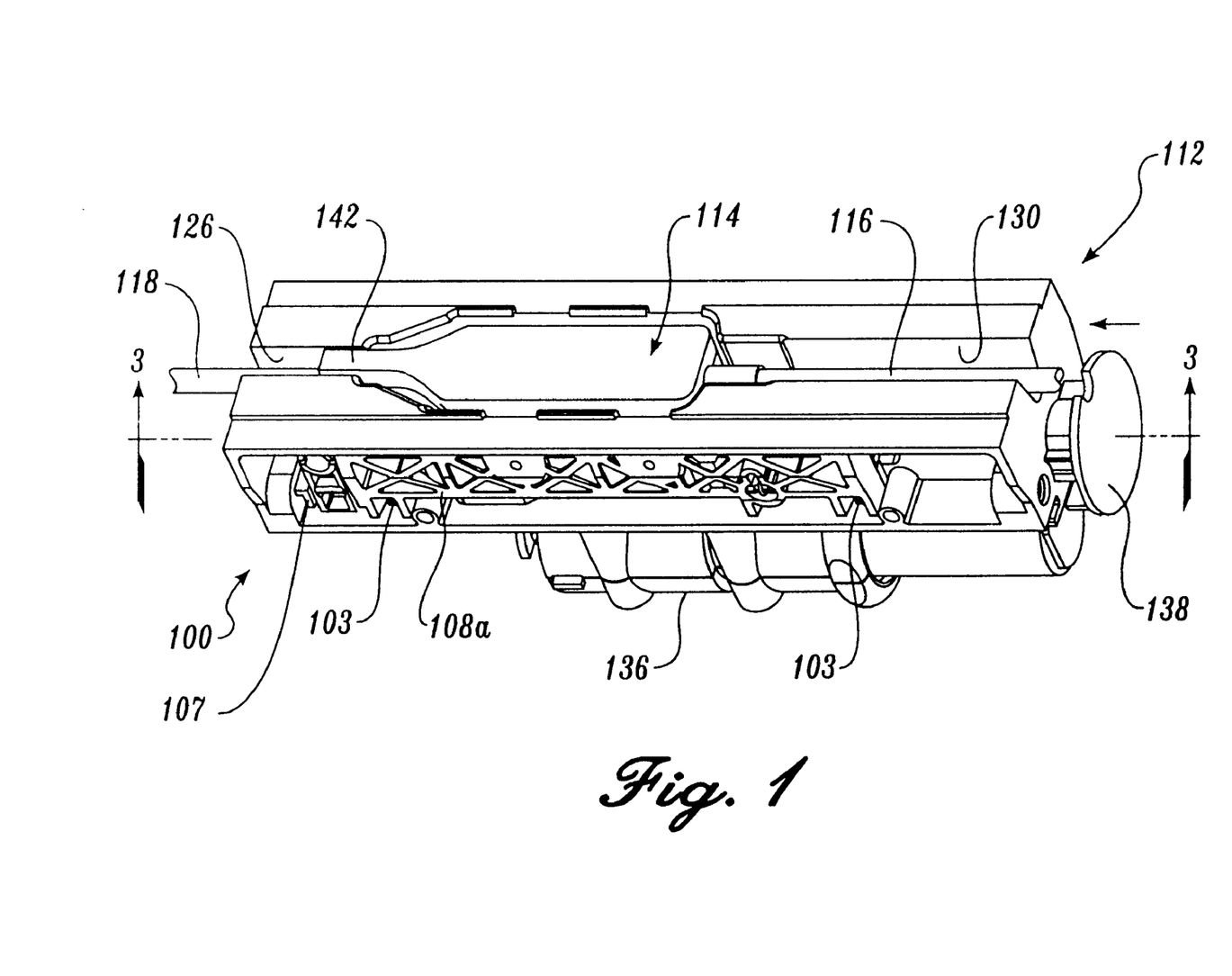
FIG. 1 is an isometric view of a pumping cassette latched within a cavity of a pump chassis in accord with the present invention.
Figure 2:
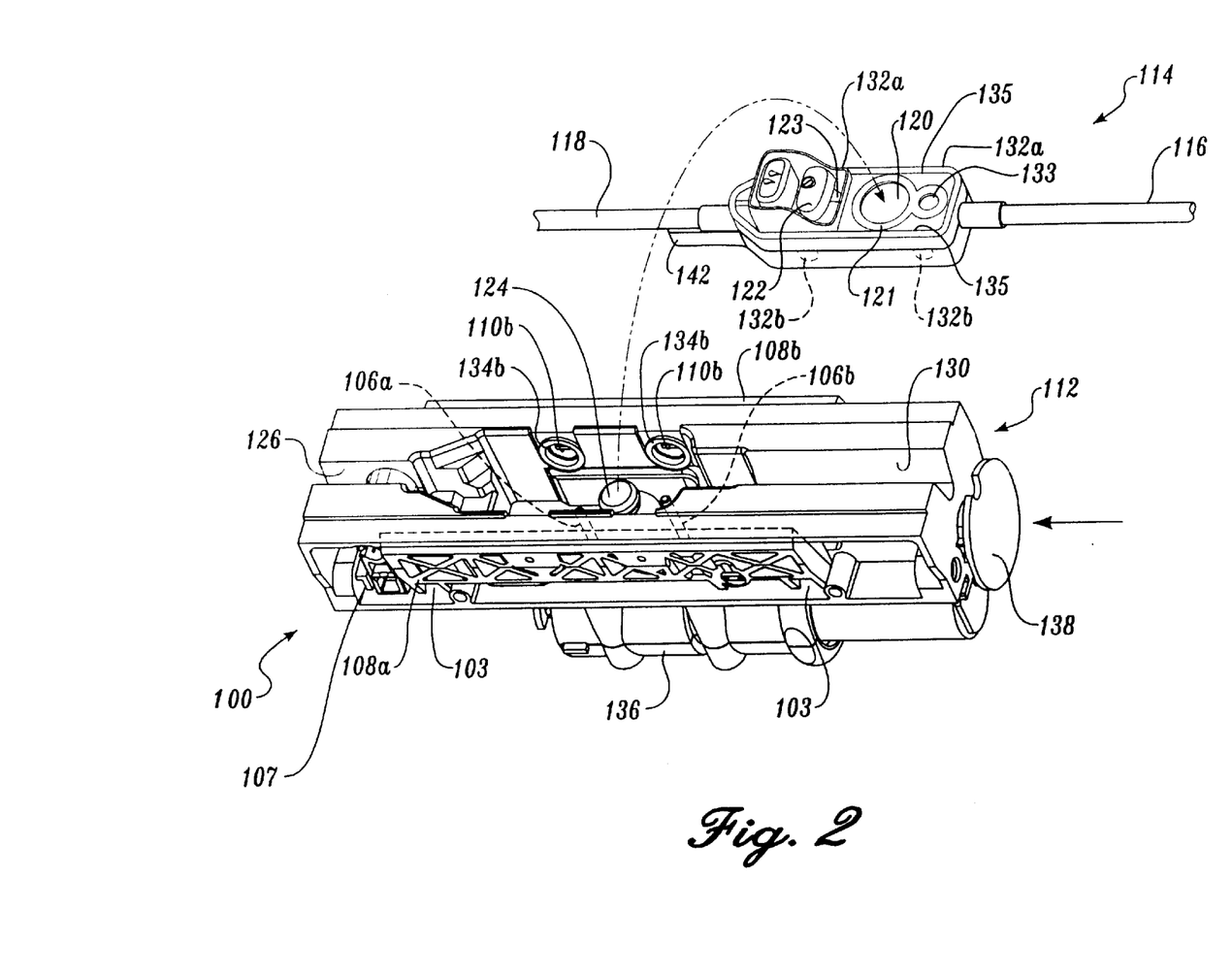
FIG. 2 is an isometric view of the pump chassis of FIG. 1, showing the pumping cassette removed from the cavity by depressing a release button.

FIGS. 1–7 display an intravenous pump assembly 100 that includes a pumping cassette 114 for forcing liquid to flow through an IV line, which comprises proximal tubing 116 and distal tubing 118 to which the pumping cassette is coupled in fluid communication. As shown in FIG. 2, pumping cassette 114 includes a flow stop 122, and an elastomeric membrane 120 that is visible through a port 121 and a port 133. A tang 142, which is disposed on the lower portion of the pumping cassette, at its distal end, facilitates positioning and guiding distal tubing 118 into a slot 126, also disposed at the distal end of a pump chassis 112, as the pumping cassette is inserted in the slot and engaged by the pump chassis.

As pumping cassette 114 is engaged within pump chassis 112, a reciprocating plunger 124 in the pump chassis bears against the surface of elastomeric membrane 120; similarly, a rod 106a contacts flow stop 122 at a nib 123, and a rod 106b is brought into contact with the surface of the elastomeric membrane that is accessed through port 133. An electric motor 136 is coupled to a drive shaft (not shown) that reciprocatively drives plunger 124 against elastomeric membrane 120 as the motor rotates a cam (not shown), which is coupled to the plunger.

An elongate shaped member 108a extends generally parallel to the longitudinal axis of pump chassis 112, on one side thereof, and a pair of latches 110a (shown in FIG. 5) are disposed on an inwardly facing surface of the member. Member 108a is pivotally connected to pump chassis 112 by a pair of hinges 103 that are disposed at opposed ends of the member's bottom edge. Similarly, an elongate shaped member 108b extends generally parallel to the longitudinal axis of pump chassis 112, at an opposite side of pump chassis 112 from member 108a, and a pair of latches 110b are disposed on an inwardly facing surface of member 108b. Member 108b is pivotally connected to the pump chassis by a pair of hinges 103 (see FIG. 7—only one of each pair shown therein). Proximal helical spring 128 and distal helical spring 131 (both partially shown in FIG. 3) extend transversely through pump chassis 112, between bars 129 on members 108a and 108b, and between bars 137 on an air bubble sensor 107, respectively, to provide a force tending to bias members 108a and 108b inwardly towards the center of the pump chassis. The air bubble sensor includes an ultrasonic transmitter and an ultrasonic receiver (not separately identified), and distal helical spring 131 extends between the ultrasonic transmitter and ultrasonic receiver, which are mounted on opposite members 108a and 108b.

The pair of latches 110b are positioned within a pair of ports 134b that are disposed in a side wall of pump chassis 112. Similarly, the pair of latches 110a are positioned within a pair of ports 134a (shown in FIGS. 5 and 6) that are disposed in an opposite side wall of pump chassis 112. Latches 110a and 110b are each beveled on their upwardly facing surface, forming a ramp on each latch that enables the sides of the pumping cassette to force the latches and associated members outwardly as the pumping cassette is pushed into and seated within the cavity of the pump chassis.

After pumping cassette 114 has been fully inserted into pump chassis 112, the pairs of latches 110a and 110b extend from within respective ports 134a and 134b, so that the latches overlie an edge 135 of the pumping cassette, locking the pumping cassette within the pump chassis in a predetermined position. In an earlier embodiment, which is still considered a viable alternative, the inner ends of the latches were positioned to engage pairs of notches 132a and 132b, which were formed on opposite sides of the pumping cassette, firmly holding the pumping cassette at the predetermined position within the pump chassis interior. However, the current preferred embodiment dispenses with notches 132a and 132b, thereby simplifying the configuration of the pumping cassette.

When members 108a and 108b are caused to swing outwardly, pairs of latches 110a and 110b are retracted into their respective ports 134a and 134b, disengaging the latches from pumping cassette 114 and enabling the pumping cassette to be removed from the interior of pump chassis 112. Regardless of whether latches 110a and 110b engage edge 135 or pairs of notches 132a and 132b, the disengagement of the latches in this manner releases the pumping cassette so it can be easily removed. In fact, when the latches are thus disengaged, the pumping cassette is able to fall free of the pump chassis under the force of gravity (if pump chassis 112 is oriented with pumping cassette 114 on the downwardly facing side of the pump chassis). Details of the mechanism employed to force members 108a and 108b to swing outwardly to disengage the pumping cassette from the pump chassis are discussed below.

Figure 3:
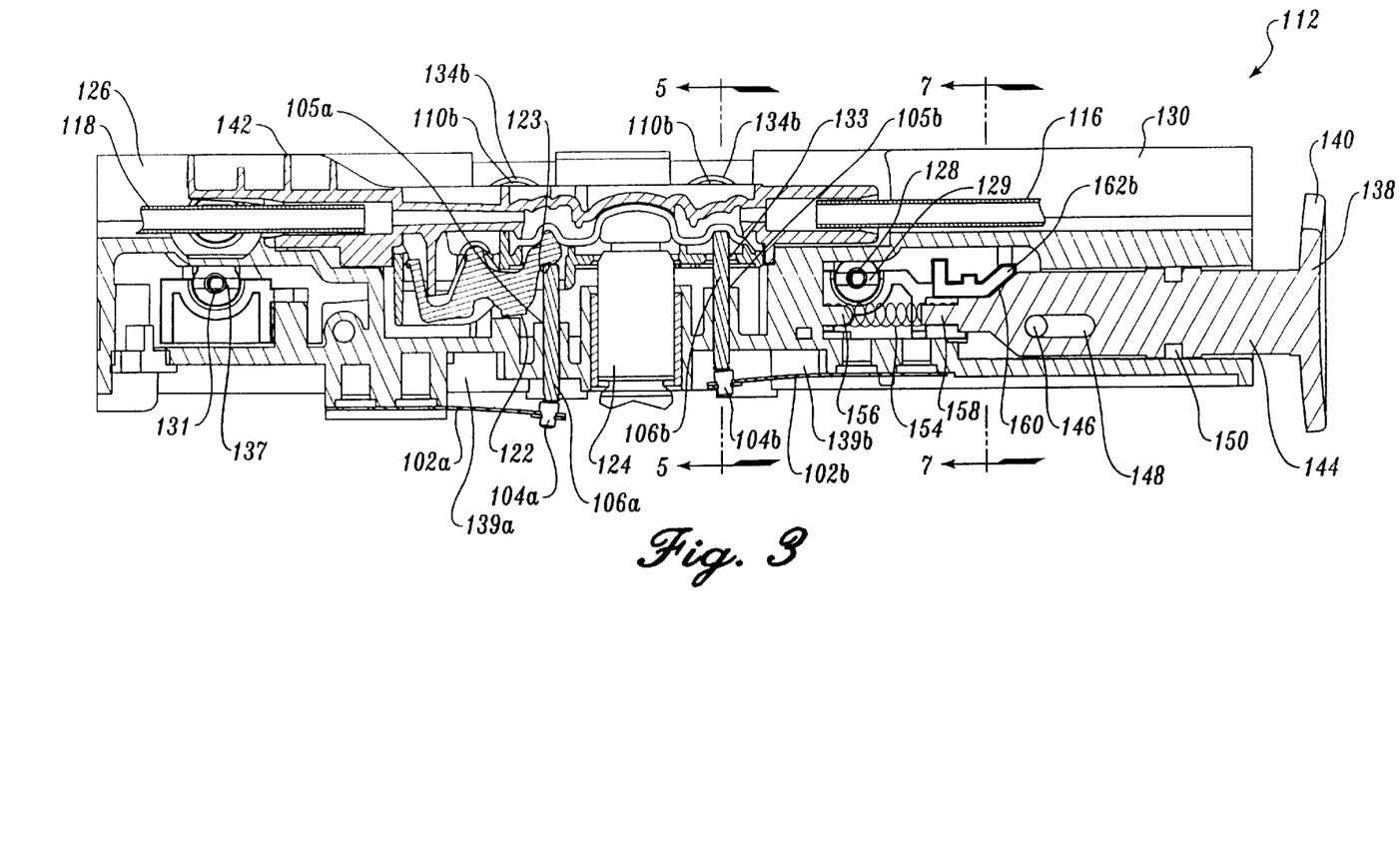
FIG. 3 is a side elevational, cross-sectional view of the pump chassis and pumping cassette of FIG. 1, taken along section lines 3—3.
Figure 4:
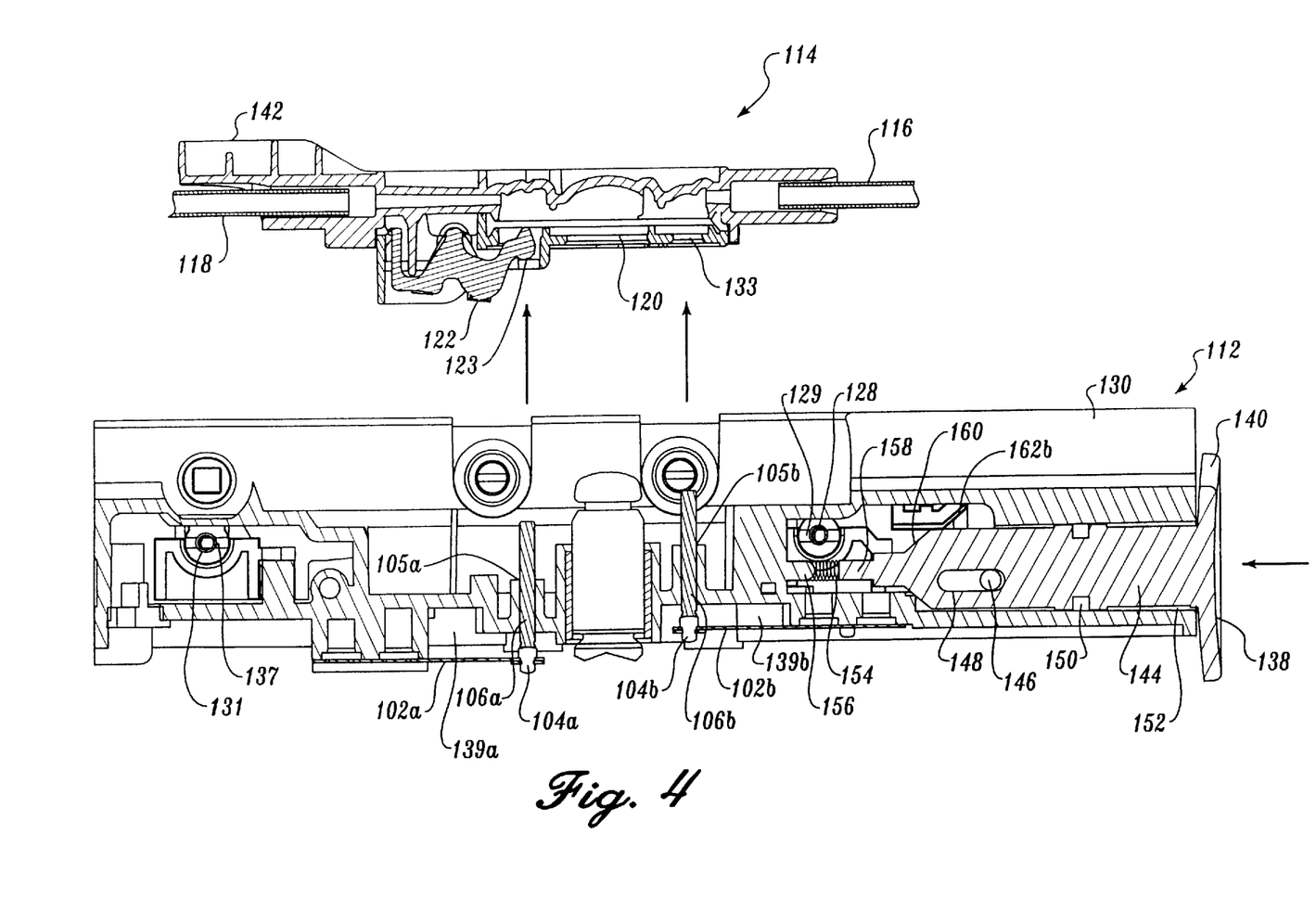
FIG. 4 is a side elevational, cross-sectional view of the pump chassis, similar to FIG. 3, but showing the pumping cassette removed from the cavity in the pump chassis.
Figure 5:
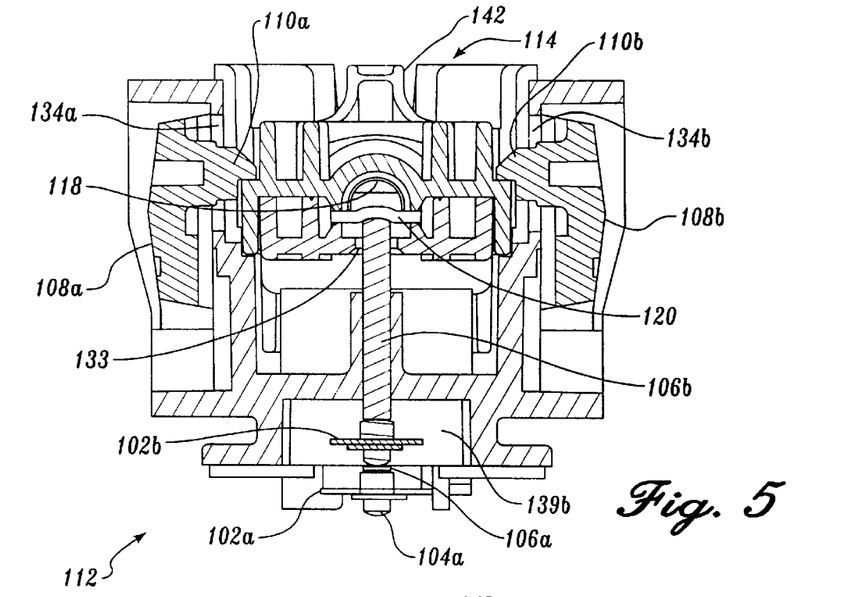
FIG. 5 is a transverse elevational, cross-sectional view of the pump chassis and pumping cassette of FIG. 3, taken along section line 5—5.
Figure 6:
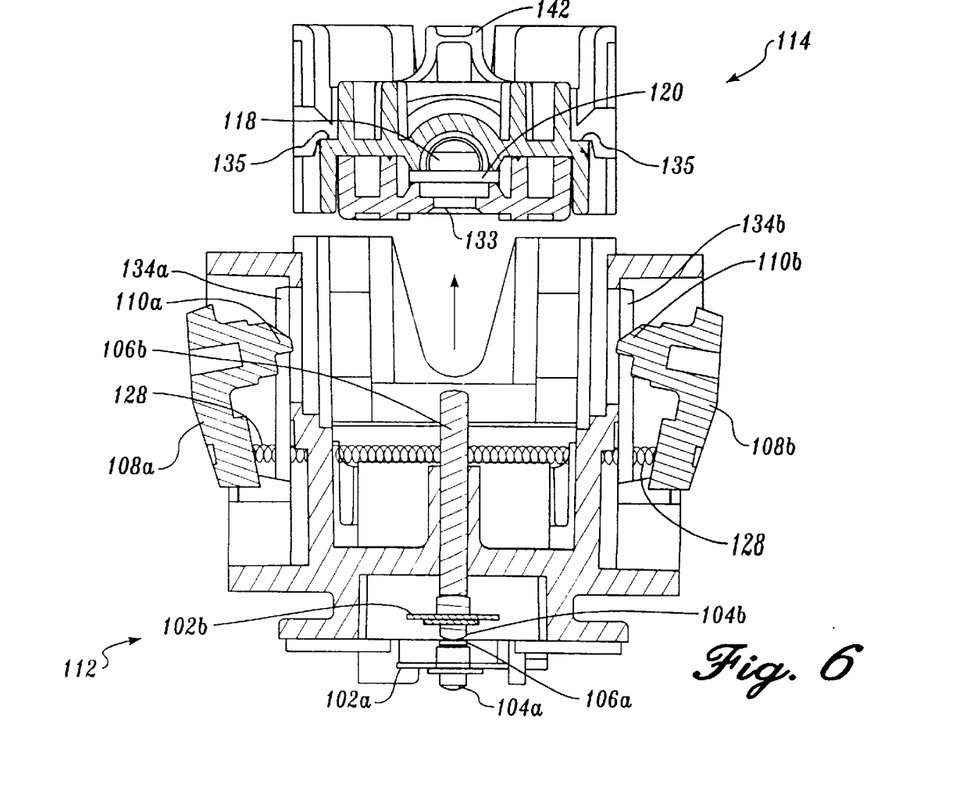
FIG. 6 is a transverse elevational, cross-sectional view of the pump chassis and pumping cassette, similar to FIG. 5, but showing the pumping cassette removed from the cavity.
Figure 7:
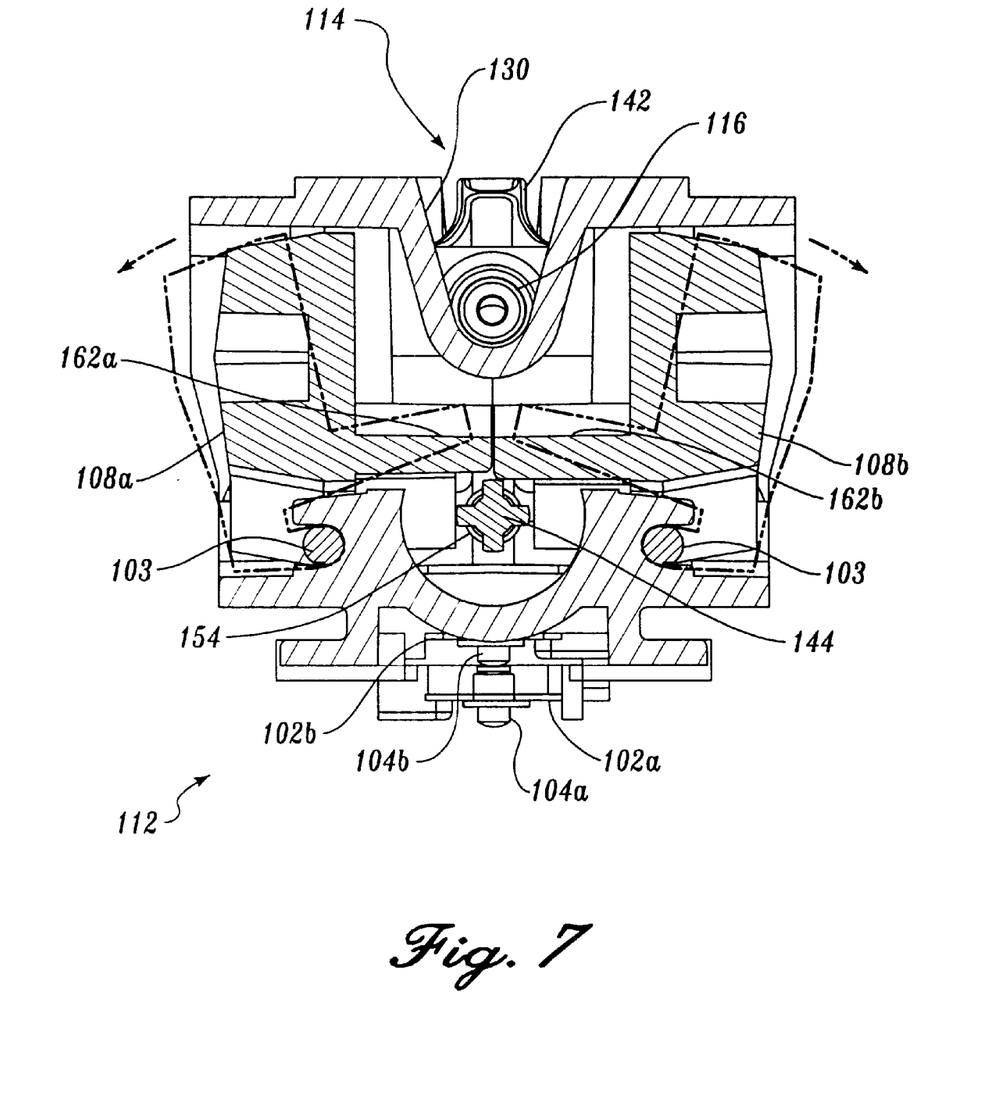
FIG. 7 is a transverse elevational, cross-sectional view of the pump chassis of FIG. 3, taken along section line 7—7.

As shown most clearly in FIGS. 3 and 4, a user actuated release button 138 is disposed at a proximal end of pump chassis 112. Release button 138 is formed on an outer end of a shaft 144 and has sufficient area to readily support the pad of a user's thumb or finger. A semicircular notch 140 is provided in a side of release button 138 to accommodate proximal tubing 116 when the pumping cassette is engaged in the pump chassis. One end of a helical spring 154 is fitted over a nib 156, and the other end of the helical spring is fitted over a tip 158 of shaft 144 within the interior of pump chassis 112. An O-ring 150 is seated around shaft 144, providing a seal around the shaft relative to a bore 152 in which shaft 144 is movably disposed. Helical spring 154 provides a biasing force against tip 158 tending to push shaft 144 out of bore 152. However, movement of shaft 144 within bore 152 is limited by a fastener 146 that extends through an elongate, longitudinally extending slot 148 formed in the shaft.

When release button 138 is pressed inwardly by a user, in the direction of the arrow as shown in FIG. 4, the force applied to the release button moves attached shaft 144 further into pump chassis 114. A ramp 160 formed on shaft 144 contacts correspondingly sloping portions of arms 162a and 162b (only arm 162b is shown in FIGS. 3 and 4) that extend transversely inwardly from members 108a and 108b, respectively. Interference between ramp 160 and arms 162a and 162b causes members 108a and 108b to pivot outwardly about their respective hinges 103, away from the interior of the pump chassis. When members 108a and 108b pivot outwardly in this manner, latches 110a and 110b move outwardly (retract) through ports 134a and 134b, so that the latches are not extended into the interior of pump chassis 112. This movement outwardly of latches 110a and 110b releases pumping cassette 114, enabling it to be removed from the pump chassis.

When pumping cassette 114 is inserted into the interior of pump chassis 112, members 108a and 108b are initially displaced outwardly by the sides of the pumping cassette forcing latches 110a and 110b out through ports 134a and 134b, respectively, until the pumping cassette seats within the pump chassis. As the pumping cassette becomes seated in place, the members are able to move towards the interior of the pump chassis, so that latches 110a and 110b engage the pumping cassette. Latches 110a and 110b engage either edges 135 in the preferred embodiment, or notches 132a and 132b, which are formed on the opposite sides of the pumping cassette, and hold the cassette at a predetermined position, as shown in FIG. 1.

In FIG. 3, pumping cassette 114 is disposed in the interior of pump chassis 112 at the predetermined position. Members 108a and 108b are shown in the position in which the pumping cassette is engaged in pump chassis 112. Membrane 120 is in contact with plunger 124, so that as the plunger is reciprocatively driven by motor 136, medicinal liquid is forced to flow through the pumping cassette. Further, rod 106b is in contact with the portion of elastomeric membrane 120 that is accessed through port 133 and rod 106a is in contact with flow stop 122, which rides on top of another portion of the elastomeric membrane in the pumping cassette. When pumping cassette 114 is thus coupled to the pump chassis, very small distal and proximal pressures within the pumping cassette are transmitted through elastomeric membrane 120 and coupled to rods 106a and 106b.

As illustrated in the Figures, a slot 130 is disposed at the proximal end of pump chassis 112 and slot 126 is disposed at the distal end of the pump chassis. Plunger 124 is positioned transversely to the interior of pump chassis 112, and the pair of latches 110b are disposed inside the pair of ports 134b. Rod 106a is 10 longitudinally disposed in a bore 1 Sa that connects the interior of chassis 112 to a cavity 139a. Rod 106a is free to move in bore 105a, with one end of the rod disposed in the chassis interior and the other end disposed in cavity 139a. The end of rod 106a is in contact with a knob 104a and applies a preload force that flexes the free end of a leaf spring 102a towards the interior of cavity 139a. Similarly, the end of rod 106b is in contact with knob 104b and applies a preload force that flexes the free end of leaf spring 102b towards the interior of cavity 139b. These preload forces stabilize the zero psig signal output from the strain gauges corresponding to a zero pressure level.

Leaf spring 102a is disposed transverse to rod 106a in cavity 139a. An end portion of leaf spring 102a is fixed to pump chassis 112 by a pair of threaded fasteners (not shown). A free end of leaf spring 102a is cantilevered from pump chassis 112 and is free to flex in a direction responsive to longitudinal movement of rod 106a. Rounded knob 104a is connected to the free end of leaf spring 102a at a position that is directly opposite the adjacent end of rod 106a. A strain gauge (not shown) is mounted on leaf spring 102a, at a middle portion of the leaf spring between its free end and its mounted end.

Similarly, rod 106b is disposed in bore 105b. An end of rod 106b is connected to a keeper 140b, which prevents the rod from slipping into the interior of the pump chassis through bore 105b. Leaf spring 102b is disposed in cavity 139b, and an end portion of the leaf spring is connected to pump chassis 112 by a pair of threaded fasteners (not shown). A free end of leaf spring 102b is cantilevered from the pump chassis and is free to flex in a direction responsive to longitudinal movement of rod 106b. Rounded knob 104b is connected to the free end of the leaf spring, at a position opposite the adjacent end of rod 106b. A strain gauge (not shown) is mounted on a middle portion of leaf spring 102b, between its free end and its mounted end.

FIG. 4 depicts pumping cassette 114 disposed adjacent to pump chassis 112, as it would be after the pumping cassette has been disengaged from the pump chassis. This Figure also shows how flow stop 122, the elastomeric membrane visible in a port 127 and in port 133 are aligned with rod 106a, plunger 124, and rod 106b, respectively. Flow stop 122 is illustrated in a closed position that disables free flow of liquid through pumping cassette 114. The pairs of latches 110a and 110b are retracted within the pairs of ports 134a and 134b that are disposed in the side walls of pump chassis 112. Note that the other ends of rods 106a and 106b are not preloaded (pressed) against the surface of knobs 104a and 104b, respectively. Further, the free ends of leaf springs 102a and 102b are disposed opposite to and extend substantially normal to rods 106a and 106b, respectively.

An advantage of the latching system for engaging pumping cassette 114 within pump chassis 112 is that it enables the pumping cassette to be firmly held in the predetermined position with almost no free play. It is important that different pumping cassettes be latched into the same predetermined position to minimize variations in the pumping characteristics of the pump chassis. Providing a positive engagement of the pumping cassette with the pump chassis by simply depressing the pumping cassette within the cavity provided in the pump chassis permits the user to install the pumping cassette with only one hand, in an extremely simple operation. Similarly, release button 136 can be depressed with one finger to quickly and conveniently release the pumping cassette from engagement with the pump chassis.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for engaging a pumping cassette at a predefined position within a pump chassis that is used to deliver fluids to a patient, comprising:

(a) a pivotable member disposed at a side of a cavity within the pump chassis, said cavity being sized to receive a pumping cassette, said pivotable member being pivotally mounted to the pump chassis so as to pivot away from and towards the cavity and including a surface configuration that engages a portion of a pumping cassette in the predefined position within the cavity; and (b) a spring coupled to said pivotable member, said spring applying a biasing force tending to pivot said pivotable member towards the cavity, so that as a pumping cassette is forced into the cavity, said pivotable member is pivoted away from the cavity, said biasing force causing said surface configuration of the pivotable member to engage the pumping cassette after it has been forced into the cavity, retaining the pumping cassette at the predefined position.

2. The apparatus of claim 1, further comprising a release that acts against said pivotable member, activation of said release by an operator causing said pivotable member to pivot away from the cavity to disengage from any pumping cassette previously retained in the cavity, to permit its removal.

3. The apparatus of claim 2, wherein said release comprises a push button extending into the pump chassis, said push button being activated by depressing it towards the pump chassis.

4. The apparatus of claim 3, wherein the release further comprises a tension spring coupled to the push button and producing a force tending to bias the push button outwardly from the pump chassis.

5. The apparatus of claim 1, wherein the surface configuration of the pivotable member comprises at least one tab adapted to engage a corresponding slot in a pumping cassette.

6. The apparatus of claim 1, wherein the surface configuration of the pivotable member comprises at least one tab adapted to overlie an edge of a pumping cassette.

7. The apparatus of claim 1, further comprising an air bubble sensor disposed on the pivotable member, said air bubble sensor pivoting with the pivotable member and thereby being adapted to pivot into contact with a tube connected to a pumping cassette that is retained in the cavity by the pivotable member.

8. The apparatus of claim 7, wherein the air bubble sensor comprises an anchor for one end of the spring.

9. Apparatus for engaging a pumping cassette at a predefined position within a pump chassis that is used to deliver fluids to a patient, comprising:
(a) a pair of opposed pivotable members disposed at opposite sides of a cavity within the pump chassis, said cavity being sized to receive a pumping cassette, each of said pair of opposed members being pivotally mounted to the pump chassis so as to pivot away from and towards the cavity and including a surface configuration that engages a portion of a pumping cassette, retaining the cassette in the predefined position within the cavity; and
(b) at least one spring coupled to said pair of opposed members, said at least one spring applying a biasing force tending to pivot said pair of opposed members towards the cavity, so that as a pumping cassette is forced into the cavity, the opposed members are pivoted outwardly, away from each other and from the cavity, said biasing force causing said surface configuration on each of the pair of opposed members to engage the pumping cassette after it has been forced into the cavity, retaining the pumping cassette at the predefined position.

10. The apparatus of claim 9, further comprising a release that when activated by an operator, forces the pair of opposed members to pivot outwardly, away from the cavity, thereby releasing any pumping cassette that has previously been inserted and retained in the cavity.

11. The apparatus of claim 10, wherein the release comprises a push button that is activated by depressing the push button.

12. The apparatus of claim 11, wherein the release further comprises a tension spring coupled to the push button and producing a force tending to bias the push button outwardly from the pump chassis.

13. The apparatus of claim 9, wherein the spring extends between the pair of opposed members.

14. The apparatus of claim 9, wherein the surface configuration on each of the pair of opposed members comprises at least one tab adapted to engage a corresponding slot in a pumping cassette as the pumping cassette is pushed into the cavity.

15. The apparatus of claim 9, wherein the surface configuration on each of the pair of opposed members comprises at least one tab adapted to overlie an edge of a pumping cassette as the pumping cassette is pushed into the cavity.

16. The apparatus of claim 9, further comprising an air bubble sensor disposed on the pair of opposed members, said air bubble sensor pivoting with the pair of opposed members and thereby being adapted to pivot into contact with a tube connected to a pumping cassette that is retained in the cavity by the pair of opposed members.

17. The apparatus of claim 16, wherein the air bubble sensor comprises an anchor for an end of said at least one spring.

18. The apparatus of claim 17, wherein a plurality of spaced-apart tabs are disposed on an inwardly facing surface of each of the pair of opposed members.

19. Apparatus for retaining a pumping cassette at a predefined position within a pump chassis, comprising:
(a) a pair of elongate members, each pivotally mounted by a pivot hinge to the pump chassis, and extending generally along opposite sides of a cavity that is sized to receive a pumping cassette, said pair of elongate members pivoting inwardly and outwardly of the cavity around the pivot hinge;
(b) a spring coupled to the pair of elongate members to apply a biasing force that tends to pivot the pair of elongate members towards each other and the cavity; and
(c) a pair of tabs disposed on each of the elongate members, said tabs having an angled surface that initially contacts a pumping cassette being pushed into the cavity, so that the pumping cassette slides along the angled surface, forcing the pair of elongate members apart as the pumping cassette is forced into the cavity, said pair of tabs engaging a pumping cassette to retain it within the cavity as the pumping cassette seats in the predefined position.

20. The apparatus of claim 19, wherein the spring extends between the pair of elongate members.

21. The apparatus of claim 19, further comprising a push button release disposed at one end of the pump chassis and extending outwardly from said one end, said push button release acting against the pair of elongate members, so as to force said pair of elongate members outwardly, disengaging a pumping cassette being retained within the cavity, when the push button release is actuated by an operator depressing it.

22. The apparatus of claim 19, further comprising an ultrasonic transmitter and an ultrasonic receiver mounted on the pair of elongate members and employed to sense air bubbles in a tube coupled to a pumping cassette that is being retained in the cavity of pump chassis.

23. The apparatus of claim 22, wherein the spring extends between the ultrasonic transmitter and the ultrasonic receiver.

24. Apparatus for engaging a pumping cassette at a predefined position within a pump chassis that is used to deliver fluids to a patient, comprising:
(a) a pivotable member disposed at a side of a cavity within the pump chassis, said cavity being sized to receive a pumping cassette, said pivotable member being pivotally mounted to the pump chassis so as to pivot away from and towards the cavity and including a surface configuration that engages a portion of a pumping cassette in the predefined position within the cavity; and (b) a biasing element coupled to said pivotable member, said biasing element applying a biasing force tending to pivot said pivotable member towards the cavity, so that as a pumping cassette is forced into the cavity, said pivotable member is pivoted away from the cavity, said biasing force causing said surface configuration of the pivotable member to engage the pumping cassette after it has been forced into the cavity, retaining the pumping cassette at the predefined position.

25. The apparatus of claim 24 wherein said biasing element is a spring.

* * * * *